United States Patent
Kanno et al.

(10) Patent No.: US 11,911,228 B2
(45) Date of Patent: *Feb. 27, 2024

(54) AQUEOUS SOLUTION FOR USE IN CLEANING VIA IRRADIATION BY ULTRAVIOLET RAYS AND/OR NEAR-ULTRAVIOLET VISIBLE LIGHT AND/OR LIGHT IN 800-900 NM NEAR-INFRARED REGION, DENTIFRICE INCLUDING SAID SOLUTION, DENTAL TREATMENT DEVICE, TOOTHBRUSH, AND TOOTH CLEANING METHOD

(71) Applicant: Luke Co., Ltd., Miyagi (JP)

(72) Inventors: Taro Kanno, Sendai (JP); Yoshimi Niwano, Osakasayama (JP); Keisuke Nakamura, Sendai (JP)

(73) Assignee: Luke Co., Ltd. (JP)

( * ) Notice: Subject to any disclaimer, the term of this patent is extended or adjusted under 35 U.S.C. 154(b) by 0 days.

This patent is subject to a terminal disclaimer.

(21) Appl. No.: 17/970,639

(22) Filed: Oct. 21, 2022

(65) Prior Publication Data

US 2023/0038203 A1 Feb. 9, 2023

Related U.S. Application Data

(62) Division of application No. 16/302,516, filed as application No. PCT/JP2017/018413 on May 16, 2017, now Pat. No. 11,510,752.

(30) Foreign Application Priority Data

May 19, 2016 (JP) .................... 2016-100826

(51) Int. Cl.
*A61C 1/00* (2006.01)
*A01N 25/22* (2006.01)
(Continued)

(52) U.S. Cl.
CPC .......... *A61C 1/0076* (2013.01); *A01N 25/22* (2013.01); *A01N 59/00* (2013.01); *A46B 15/00* (2013.01);
(Continued)

(58) Field of Classification Search
CPC .. A61L 2/10; A61L 2/085; A61K 8/22; A61K 33/40; A01N 59/00; A01N 25/22;
(Continued)

(56) References Cited

U.S. PATENT DOCUMENTS 3,341,384 A 9/1967 Alderuccio et al.
5,360,338 A 11/1994 Waggoner
(Continued)

FOREIGN PATENT DOCUMENTS

JP H06-183942 A 7/1994
JP H08-503388 A 4/1996
(Continued)

OTHER PUBLICATIONS

Patterson et al., "The mineral content of tap water | United States households", Journal of Food Composition and Analysis, 31(2013) 46-50. (Year: 2013).*

(Continued)

*Primary Examiner* — Jianfeng Song
(74) *Attorney, Agent, or Firm* — Harness, Dickey & Pierce, P.L.C.

(57) ABSTRACT

An aqueous solution for intraoral cleaning via irradiation with ultraviolet ray and/or near-ultraviolet visible ray and/or ray in an 800-900 nm near-infrared region is employed as the hydrogen peroxide aqueous solution, wherein a concentration of hydrogen peroxide is 1 w/v % to 7 w/v %, and a concentration of a hydrogen peroxide stabilizer is 81 ppm (mg/L) or less in the aqueous solution.

3 Claims, 10 Drawing Sheets

(51) Int. Cl.
*A01N 59/00* (2006.01)
*A46B 15/00* (2006.01)
*A61C 17/00* (2006.01)
*A61K 8/22* (2006.01)
*A61K 33/40* (2006.01)
*A61L 2/18* (2006.01)
*A61N 5/06* (2006.01)
*A61C 17/02* (2006.01)
*A61C 19/06* (2006.01)
*A61L 2/08* (2006.01)
*A61L 2/10* (2006.01)
*A61Q 11/00* (2006.01)

(52) U.S. Cl.
CPC .............. *A61C 17/00* (2013.01); *A61K 8/22* (2013.01); *A61K 33/40* (2013.01); *A61L 2/186* (2013.01); *A61N 5/0603* (2013.01); *A61C 1/0084* (2013.01); *A61C 17/02* (2013.01); *A61C 19/06* (2013.01); *A61L 2/085* (2013.01); *A61L 2/10* (2013.01); *A61N 2005/0606* (2013.01); *A61Q 11/00* (2013.01)

(58) Field of Classification Search
CPC ....... A61C 19/06; A61C 1/0076; A61C 17/00; A61C 1/0084; A61N 2005/0606; A61N 5/0603; A61Q 11/00; A46B 15/00
See application file for complete search history.

(56) References Cited

U.S. PATENT DOCUMENTS

| 2004/0106081 | A1* | 6/2004 | Karazivan .............. A61C 17/20 433/29 |
| 2005/0227201 | A1* | 10/2005 | Pond .................... A61C 1/0084 433/119 |
| 2007/0166398 | A1 | 7/2007 | Bobbert |
| 2009/0074881 | A1* | 3/2009 | Kielbania, Jr. ........ A01N 37/36 424/618 |
| 2017/0156834 | A1 | 6/2017 | Kanno et al. |

FOREIGN PATENT DOCUMENTS

| JP | 3069049 U | 5/2000 |
| JP | 2007-167088 A | 7/2007 |
| JP | 2008-284312 A | 11/2008 |
| JP | 2012-082182 A | 4/2012 |
| WO | 2010-054098 A2 | 5/2010 |
| WO | 2015-170381 A1 | 11/2015 |

OTHER PUBLICATIONS

Kanno, Kai, H., et al:, "New Irradiation System for Clinical Dental Treatment Advanced Using Low Density Hydrogen Peroxide and Laser Diode", Scientific Meeting of Japan Prosthodontic Society (Jun. 2008), vol. 117th, p. 194.
European Office Action for corresponding Application No. 17799398.7 dated Nov. 20, 2020 (3 pages).

* cited by examiner

Phenacetin concentration 81 ppm, before laser irradiation

Phenacetin concentration 81 ppm, after irradiation for 5 minutes

Phenacetin concentration 334 ppm, before laser irradiation

Phenacetin concentration 334 ppm, after irradiation for 5 minutes

Acetanilide concentration 177 ppm, before laser irradiation

Acetanilide concentration 177 ppm, after irradiation for 5 minutes

AQUEOUS SOLUTION FOR USE IN CLEANING VIA IRRADIATION BY ULTRAVIOLET RAYS AND/OR NEAR-ULTRAVIOLET VISIBLE LIGHT AND/OR LIGHT IN 800-900 NM NEAR-INFRARED REGION, DENTIFRICE INCLUDING SAID SOLUTION, DENTAL TREATMENT DEVICE, TOOTHBRUSH, AND TOOTH CLEANING METHOD

CROSS REFERENCE TO RELATED APPLICATIONS

This application is a divisional application of U.S. application Ser. No. 16/302,516 filed Nov. 16, 2018, which is a National Stage Application of PCT/JP2017/018413 filed on May 16, 2017 and published in Japanese as WO/2017/199974 A1 on Nov. 23, 2017 which claims priority to Japanese Patent Application No. JP-2016-100826 filed on May 19, 2016. All of the above applications are hereby expressly incorporated by reference herein in their entireties.

BACKGROUND

Technical Field

The present invention relates to an intraoral cleaning technique.

Related Art

Various techniques have been conventionally proposed as intraoral cleaning techniques. For example, a technique of simultaneous irradiation with hydrogen peroxide aqueous solution as well as ultraviolet ray and/or near-ultraviolet visible ray and/or ray in an 800-900 nm near-infrared region from a tip of a scaler tip in a dental treatment apparatus to sterilize periodontal disease bacteria and the like, has been published.

This principle is that hydrogen peroxide is decomposed in an oral cavity by irradiating hydrogen peroxide with ultraviolet ray and/or near-ultraviolet visible ray and/or ray in the 800-900 nm near-infrared region, so that a hydroxyl radical is generated to sterilize periodontal disease bacteria and the like.

The technique described in Japanese Patent Laid-Open No. 2012-82182 is intended to sterilize by decomposing hydrogen peroxide via irradiation with ultraviolet ray to generate hydroxy radicals, but ultraviolet ray is known to decompose not only hydrogen peroxide but also many kinds of substances. The above description also applies to near-ultraviolet visible ray. Also, the hydroxyl radicals generated by decomposing hydrogen peroxide are known to decompose many kinds of substances by its strong oxidizing power.

Incidentally, a general hydrogen peroxide aqueous solution contains a stabilizer due to instability of hydrogen peroxide. When such a hydrogen peroxide aqueous solution containing the stabilizer is used for dental treatment of periodontal disease or the like, not only hydrogen peroxide but also this stabilizer are irradiated with ultraviolet ray and/or near-ultraviolet visible ray and/or ray in an 800-900 nm near-infrared region emitted from a scaler tip, and thus an unexpected substance may be generated. In addition, as described above, the hydroxyl radical generated by decomposition of hydrogen peroxide may also react with the stabilizer to generate an unexpected substance. For example, carcinogenic chemical substances and other chemical substances harmful to human body may be generated by decomposition of the contained stabilizer or the like, and it is preferable that such a risk is reduced as much as possible.

SUMMARY

In order to solve the above problems, the present inventor has invented, as the first invention, a hydrogen peroxide aqueous solution in which a stabilizer contained in the hydrogen peroxide aqueous solution is reduced to 81 ppm (mg/L) or less in the aqueous solution, which is considered to be a safe range, for cleaning via irradiation with ultraviolet ray and/or near-ultraviolet visible ray and/or ray in an 800-900 nm near-infrared region.

As the second invention, the inventor has invented the aqueous solution for intraoral cleaning via irradiation with ultraviolet ray and/or near-ultraviolet visible ray and/or ray in the 800-900 nm near-infrared region, wherein a concentration of hydrogen peroxide is 2 w/v % to 6 w/v %, on the basis of the first invention.

As the third invention, the inventor has invented the aqueous solution for intraoral cleaning via irradiation with ultraviolet ray and/or near-ultraviolet visible ray and/or ray in the 800-900 nm near-infrared region, wherein the hydrogen peroxide stabilizer is any one or more of phosphoric acid, phenacetin and acetanilide, on the basis of the first and second inventions.

As the fourth invention, the inventor has invented the aqueous solution for intraoral cleaning via irradiation with ultraviolet ray and/or near-ultraviolet visible ray and/or ray in the 800-900 nm near-infrared region, wherein a content of impurity heavy metals is only 0.001 w/v % or less with respect to hydrogen peroxide, on the basis of the first to third inventions.

Furthermore, as the fifth invention, the inventor has invented a dentifrice for cleaning via irradiation with ultraviolet ray and/or near-ultraviolet visible ray and/or ray in the 800-900 nm near-infrared region, comprising a dentifrice base, hydrogen peroxide in an amount of 1 w/v % to 7 w/v % with respect to the dentifrice base, and the hydrogen peroxide stabilizer in an amount of only 81 ppm (mg/L) or less with respect to the base.

As the sixth invention, the inventor has invented the dentifrice for cleaning via irradiation with ultraviolet ray and/or near-ultraviolet visible ray and/or ray in the 800-900 nm near-infrared region, wherein the concentration of hydrogen peroxide is 2 w/v % to 6 w/v %, on the basis of the fifth invention.

As the seventh invention, the inventor has invented the dentifrice for cleaning via irradiation with ultraviolet ray and/or near-ultraviolet visible ray and/or ray in the 800-900 nm near-infrared region, wherein the hydrogen peroxide stabilizer is any one or more of phosphoric acid, phenacetin and acetanilide, on the basis of the fifth and sixth inventions.

As the eighth invention, the inventor has invented the dentifrice for cleaning via irradiation with ultraviolet ray and/or near-ultraviolet visible ray and/or ray in the 800-900 nm near-infrared region, wherein a content of impurity heavy metals is only 0.001 w/v % or less with respect to hydrogen peroxide, on the basis of the fifth to seventh inventions.

Furthermore, as the ninth invention, the inventor has invented a dental treatment apparatus comprising a scaler tip which injects the aqueous solution for intraoral cleaning via irradiation with ultraviolet ray and/or near-ultraviolet visible ray and/or ray in the 800-900 nm near-infrared region according to the first to fourth inventions, as well as ultraviolet ray and/or near-ultraviolet visible ray and/or ray in the 800-900 nm near-infrared region.

As the tenth invention, the inventor has invented the dental treatment apparatus, wherein at least an inner face of a flow pass in the scaler tip for the aqueous solution for cleaning via irradiation with ultraviolet ray and/or near-ultraviolet visible ray and/or ray in the 800-900 nm near-infrared region is a nonmetallic face, on the basis of the ninth invention.

As the eleventh invention, the inventor has invented a method for cleaning teeth, which comprises injecting the aqueous solution for cleaning via irradiation with ultraviolet ray and/or near-ultraviolet visible ray and/or ray in the 800-900 nm near-infrared region according to any one of the first to fourth inventions as well as ultraviolet ray and/or near-ultraviolet visible ray and/or ray in the 800-900 nm near-infrared region at the same time from the tip of the scaler tip.

Furthermore, as the twelfth invention, the inventor has invented a toothbrush to be used in combination with the dentifrice according to any one of the fifth to eighth inventions, comprising an ultraviolet ray- and/or near-ultraviolet visible ray- and/or 800-900 nm near-infrared region ray-emitting section for emitting ultraviolet ray and/or near-ultraviolet visible ray and/or ray in the 800-900 nm near-infrared region from a bristle area.

Advantageous Effect of the Invention

The present invention can suppress generation of substances that are carcinogenic and harmful to human bodies feared to occur in association with decomposition of a stabilizer in an oral cavity due to ultraviolet ray and/or near-ultraviolet visible ray and/or ray in the 800-900 nm near-infrared region or synthesis of another substance derived from the stabilizer, as well as decomposition of the stabilizer in the oral cavity due to the hydroxyl radical generated by decomposition of hydrogen peroxide and synthesis of another substance derived from the stabilizer, so that safer intraoral cleaning can be realized.

DETAILED DESCRIPTION

Hereinafter, embodiments of the present invention will be explained with reference to accompanying drawings. Note that, the present invention should not be limited to these embodiments at all, and the present invention can be practiced in various aspects without departing from the gist. Embodiment 1 will be explained mainly regarding inventions 1, 2, 3, 4, 9, 10 and 11. Embodiment 2 will be explained mainly regarding inventions 5, 6, 7, 8 and 12.

Embodiment 1

The aqueous solution for cleaning via irradiation with ultraviolet ray and/or near-ultraviolet visible ray and/or ray in the 800-900 nm near-infrared region is characterized in that the concentration of hydrogen peroxide is 1 w/v % to 7 w/v %, and the concentration of the hydrogen peroxide stabilizer is only 81 ppm or lower in the aqueous solution. If the concentration of hydrogen peroxide is 1 w/v % or lower, hydroxyl radicals cannot be sufficiently generated and the work efficiency of sterilization is poor, and if the concentration is 7 w/v % or higher, hydroxyl radicals are excessively generated, and thus it is difficult to store the aqueous solution with a small amount of hydrogen peroxide stabilizer while keeping its quality for about 1 to 2 days.

Figure 1:
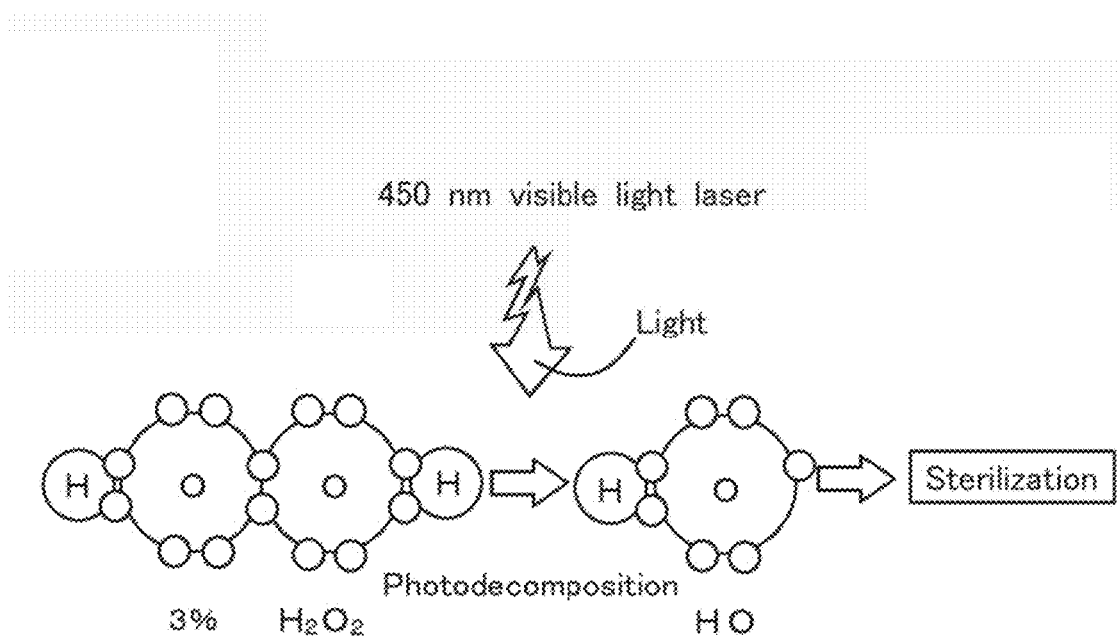
FIG. 1 illustrates a conceptual diagram of radical generation from hydrogen peroxide aqueous solution.

The aqueous solution for cleaning via irradiation with ultraviolet ray and/or near-ultraviolet visible ray and/or ray in the 800-900 nm near-infrared region in this embodiment contains hydrogen peroxide, and this hydrogen peroxide is decomposed by the hydroxy radical via irradiation with ultraviolet ray and/or near-ultraviolet visible ray and/or ray in the 800-900 nm near-infrared region to sterilize periodontal disease bacteria in the oral cavity. The sterilizing power can be regulated by combining the concentration of hydrogen peroxide and the light intensity. For example, if the concentration of hydrogen peroxide is 3 w/v %, irradiation with ultraviolet ray at around 405 nm (e.g. a range of plus/minus about 10% thereof) and/or near-ultraviolet visible ray and/or ray in the 800-900 nm near-infrared region is conceivable. Now, see FIG. 1. FIG. 1 illustrates a conceptual diagram of generation of hydroxyl radicals as sterilizing substances of the aqueous solution for cleaning via irradiation with ultraviolet ray and/or near-ultraviolet visible ray and/or ray in the 800-900 nm near-infrared region according to this embodiment.

When hydrogen peroxide ($H_2O_2$) before decomposition is irradiated with lasers of ultraviolet ray and/or near-ultraviolet visible ray and/or ray in the 800-900 nm near-infrared region, hydrogen peroxide is photodecomposed as shown by arrows and changed into HO• (HO-dot: the dot represents the presence of unpaired electron (radical)). This HO• is a structure having unpaired electron, has strong oxidizing power and sterilizes by destroying the cell membrane and the like of the targeted periodontal disease bacteria through oxidization.

On the other hand, hydrogen peroxide aqueous solution has low stability, and since hydrogen peroxide is decomposed at stages of distribution and storage, the hydrogen peroxide aqueous solution generally contains stabilizers. The stabilizers may be phosphoric acid, phenacetin, acetanilide or the like and typically contained at several hundreds ppm. This is because these stabilizers per se have low reactivity and do not affect sterilization involving hydrogen peroxide and chemical reactions such as bleaching.

However, irradiation with lasers of ultraviolet ray and/or near-ultraviolet visible ray and/or ray in the 800-900 nm near-infrared region is carried out irrespective of whether the irradiated target is hydrogen peroxide or the stabilizer. Since the lasers of ultraviolet ray and/or near-ultraviolet visible ray and/or ray in the 800-900 nm near-infrared region have high energy, they have strong abilities for decomposing chemical substances, and even a stabilizer which normally has low reactivity is decomposed and may generate an unknown substance. In addition, the hydroxyl radicals generated by irradiating hydrogen peroxide with lasers of ultraviolet ray and/or near-ultraviolet visible ray and/or ray in the 800-900 nm near-infrared region may also decompose the stabilizer with its strong oxidizing power or generate an unknown chemical substance by an unknown synthetic reaction between decomposed products.

Thus, the following experiment was carried out in order to clarify the relationship between the concentration of the hydrogen peroxide stabilizer and the presence of the decomposed products.

That is, a hydrogen peroxide aqueous solution A containing 81 ppm of phenacetin as a stabilizer, a hydrogen peroxide aqueous solution F containing 334 ppm of phenacetin as a stabilizer, and a hydrogen peroxide aqueous solution J containing 177 ppm of acetanilide as a stabilizer were irradiated with a laser beam at a wavelength of 405 nm to evaluate the presence or absence of change in HPLC chromatograms before and after the irradiation.

Figure 2:
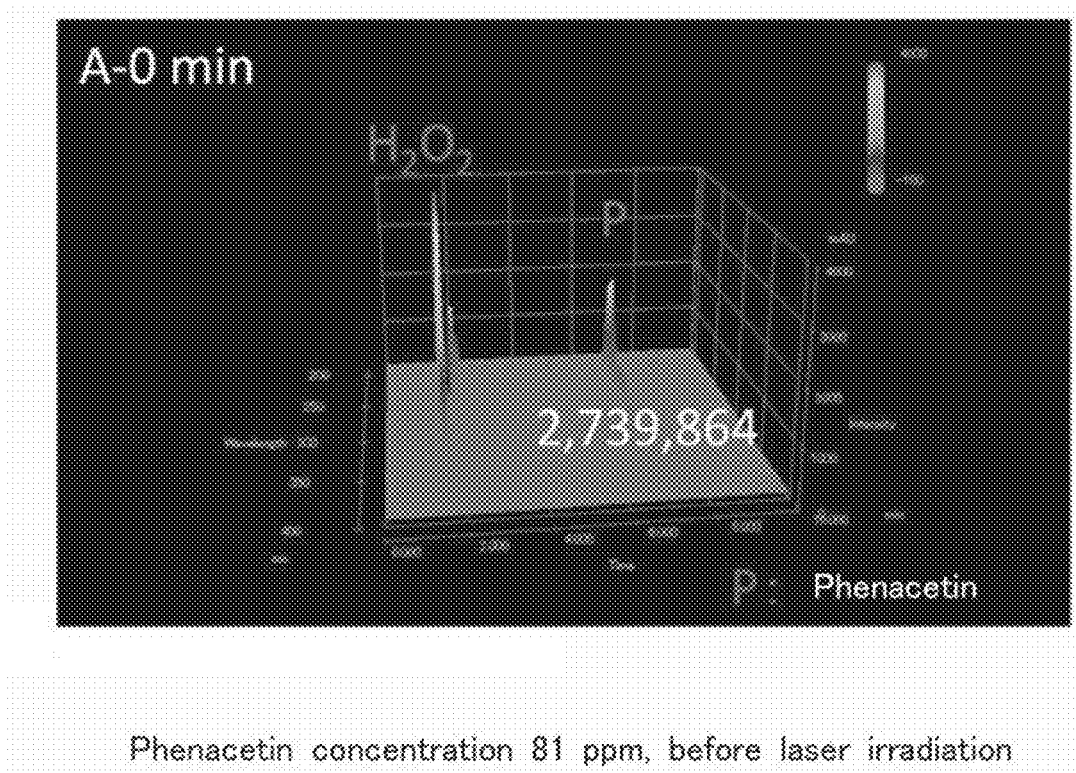
FIG. 2 illustrates a result of high performance liquid chromatography (HPLC) analysis on a hydrogen peroxide aqueous solution A containing 81 ppm of phenacetin before laser irradiation.
Figure 3:
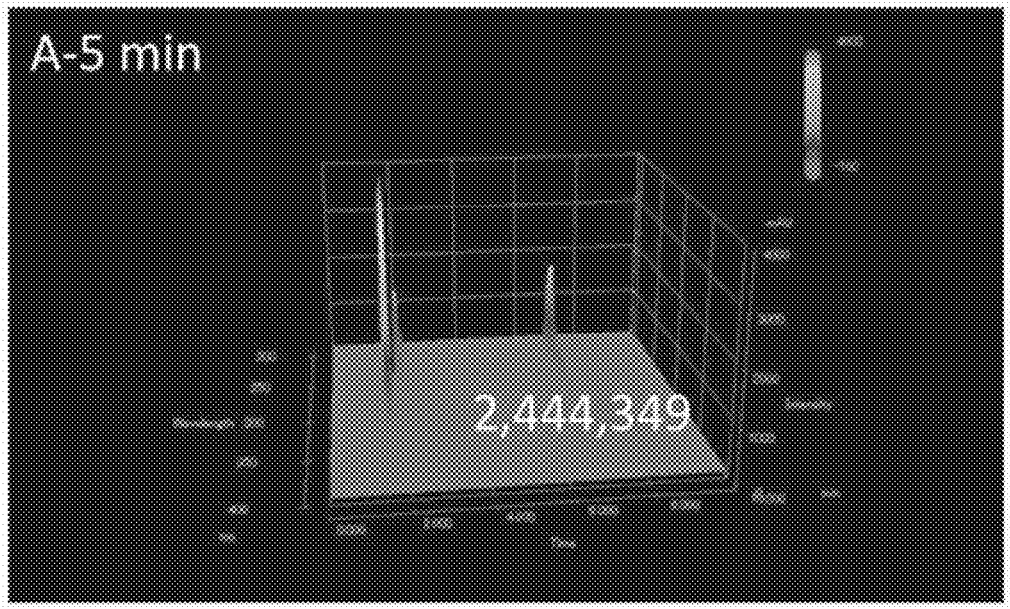
FIG. 3 illustrates a result of high performance liquid chromatography (HPLC) analysis on a hydrogen peroxide aqueous solution A containing 81 ppm of phenacetin after laser irradiation.

FIG. 2 illustrates a diagram showing the results of HPLC measurement on the aqueous solution A before the laser irradiation. It is shown that substances other than the expected hydrogen peroxide and phenacetin are not contained. FIG. 3 illustrates a diagram showing the results of HPLC measurement on the aqueous solution A after the laser irradiation for 5 minutes. As shown in FIGS. 2 and 3, no significant change was observed in the chromatogram by the laser irradiation for 5 minutes. That is, generation of a new substance has not been confirmed in the hydrogen peroxide aqueous solution A containing 81 ppm of phenacetin as a stabilizer by the laser irradiation for 5 minutes. The reason why the irradiation time is set to 5 minutes is that the continuous laser irradiation time is at most about several tens of seconds in dental treatment for periodontal disease or the like, and it is considered that if safety is confirmed through continuous laser irradiation for 5 minutes, safety in treatment is secured.

Figure 4:
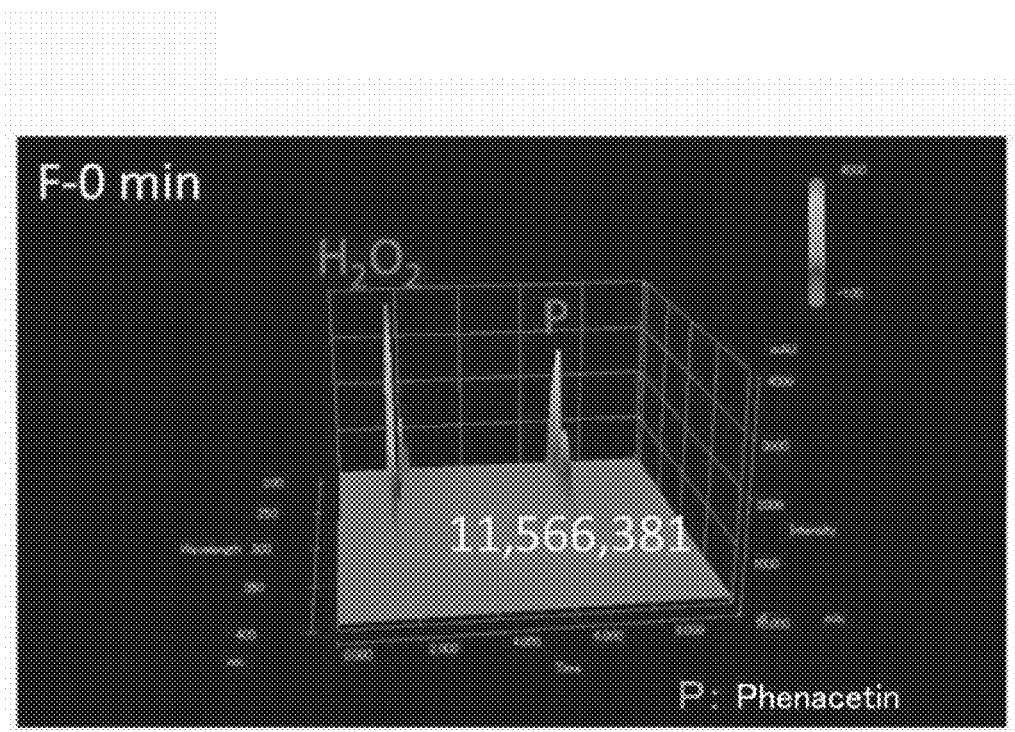
FIG. 4 illustrates a result of high performance liquid chromatography (HPLC) analysis on a hydrogen peroxide aqueous solution F containing 344 ppm of phenacetin before laser irradiation.
Figure 5:
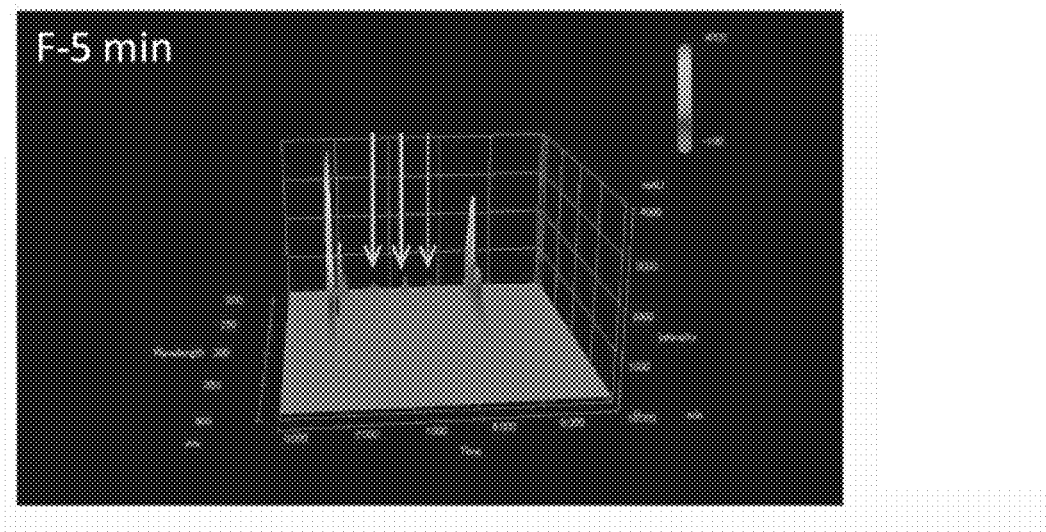
FIG. 5 illustrates a result of high performance liquid chromatography (HPLC) analysis on a hydrogen peroxide aqueous solution F containing 344 ppm of phenacetin after laser irradiation.

FIG. 4 illustrates a diagram showing the results of HPLC measurement on the hydrogen peroxide aqueous solution F containing 334 ppm of phenacetin as a stabilizer before the laser irradiation. Also for the aqueous solution F, only hydrogen peroxide and phenacetin are substances detected as inclusions before the laser irradiation. FIG. 5 illustrates a diagram showing the results of HPLC measurement on the aqueous solution F after the laser irradiation for 5 minutes. As shown in FIGS. 4 and 5, a new peak was generated in the chromatogram by laser irradiation for 5 minutes, and generation of an unknown substance which had been absent before the laser irradiation was observed in the hydrogen peroxide aqueous solution F containing 334 ppm of phenacetin as a stabilizer (arrows in FIG. 5).

Figure 6:
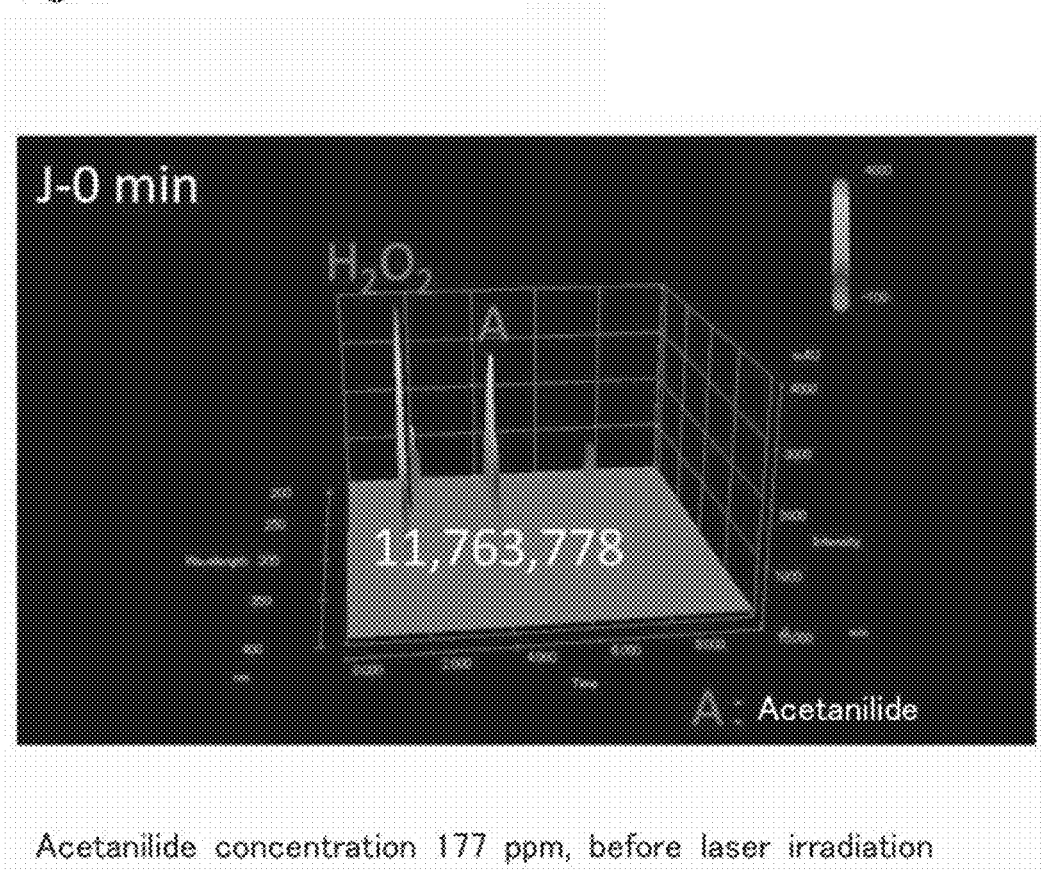
FIG. 6 illustrates a result of high performance liquid chromatography (HPLC) analysis on a hydrogen peroxide aqueous solution J containing 177 ppm of acetanilide before laser irradiation.
Figure 7:
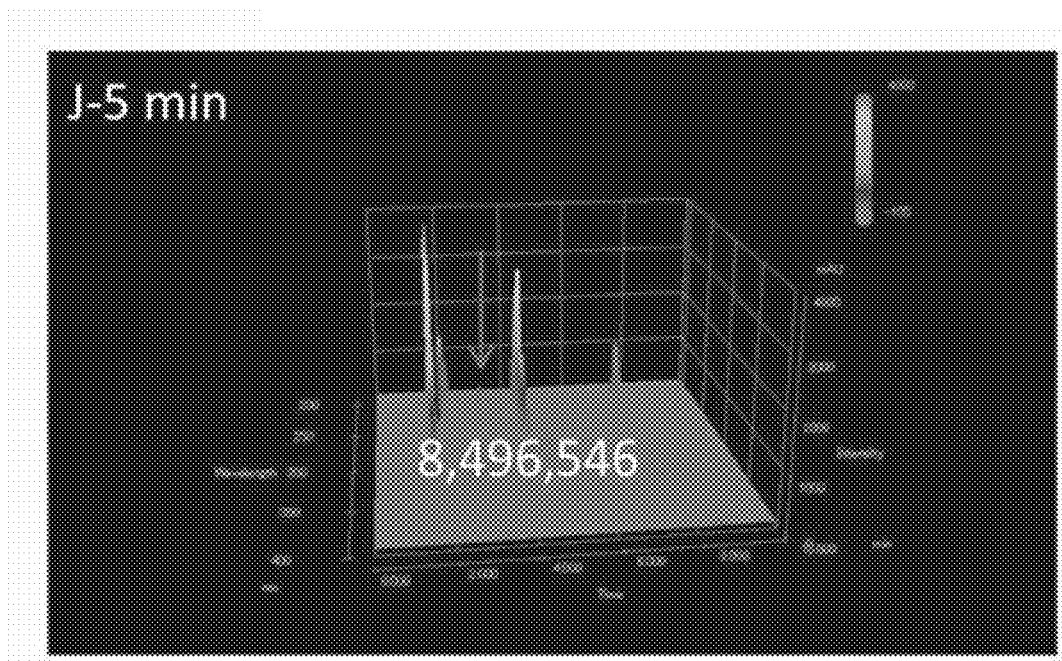
FIG. 7 illustrates a result of high performance liquid chromatography (HPLC) analysis on a hydrogen peroxide aqueous solution J containing 177 ppm of acetanilide after laser irradiation.

FIG. 6 illustrates a diagram showing the results of HPLC measurement on the hydrogen peroxide aqueous solution J containing 177 ppm of acetanilide as a stabilizer before the laser irradiation. Also for the aqueous solution J, substances other than hydrogen peroxide and acetanilide were not detected before laser irradiation. FIG. 7 illustrates a diagram showing the results of HPLC measurement on the aqueous solution J after laser irradiation for 5 minutes. As shown in FIGS. 6 and 7, a new peak was generated in the chromatogram by laser irradiation for 5 minutes, and generation of an unknown substance which had been absent before the laser irradiation was observed in the hydrogen peroxide aqueous solution J containing 177 ppm of acetanilide as a stabilizer (arrows in FIG. 7).

From the above experiments, it was shown that when the concentration of phenacetin and acetanilide as stabilizers contained in general hydrogen peroxide aqueous solution was a predetermined concentration or higher, phenacetin and acetanilide were decomposed by laser irradiation for at least 5 minutes to generate an unknown decomposed product or synthesized product. On the other hand, it was shown that when the phenacetin concentration was 81 ppm and the laser irradiation time was within 5 minutes, no decomposed product was generated.

When treatment is carried out using the aqueous solution for cleaning via irradiation with ultraviolet ray and/or near-ultraviolet visible ray and/or ray in the 800-900 nm near-infrared region according to this embodiment, the aqueous solution continues to be injected all the time, and thus the hydrogen peroxide aqueous solution does not stay in a certain place nor receive laser irradiation. Hence, if there is no change by laser irradiation for 5 minutes, it can be said that a new decomposed product is not generated also when used in clinical practice.

Consequently, it is desirable that the aqueous solution for cleaning via irradiation with ultraviolet ray and/or near-ultraviolet visible ray and/or ray in the 800-900 nm near-infrared region according to this embodiment contains no hydrogen peroxide stabilizer, but when the stabilizer is contained, its concentration is 81 ppm or lower in the aqueous solution. From the viewpoints of both the decomposed product through the reaction and the cost, the concentration of the hydrogen peroxide stabilizer is desired to be as low as possible. As the hydrogen peroxide stabilizer, it is conceivable to use any one or more of phenacetin, acetanilide and phosphoric acid.

Note that the hydrogen peroxide stabilizer is added for preventing hydrogen peroxide from being decomposed by metal ions such as iron. Thus, iron and copper in pure water used for diluting hydrogen peroxide was analyzed, and as a result, it was confirmed that both iron and copper were contained at a detection limit value (0.05 mg/L) or lower. Hydrogen peroxide aqueous solution was subjected to an acceleration test, which was prepared by diluting a stock solution of about 30 w/v % hydrogen peroxide aqueous solution containing a stabilizer at only a predetermined amount or lower stored at a cool dark place with pure water to 3 w/v %, and which contained iron and copper at a detection limit value (0.05 mg/L) or lower as well as phenacetin and acetanilide at 81 ppm (mg/L) or lower. As a result, hydrogen peroxide was stable at room temperature for 3 years.

From the viewpoint of preventing decomposition of hydrogen peroxide, it is desirable that the aqueous solution for cleaning via irradiation with ultraviolet ray and/or near-ultraviolet visible ray and/or ray in the 800-900 nm near-infrared region according to this embodiment contains no impurity heavy metal. It was checked whether impurity metals were contained in the diluted hydrogen peroxide aqueous solution, by means of an apparatus with a detection limit value of 0.05 mg/L. As a result, neither iron nor copper was detected.

Hence, even if hydrogen peroxide contains only 81 ppm or less of stabilizer, there is no problem as long as the iron and copper content is 0.05 mg/L or less.

That is, when the stabilizer content is only 81 ppm or less and the iron and copper content is 0.05 mg/L or less, the hydrogen peroxide aqueous solution can generate hydroxyl radicals in an amount sufficient for treating periodontal disease by laser irradiation with ultraviolet ray at around 405 nm (e.g. a range of plus/minus about 10%) and/or near-ultraviolet visible ray and/or ray in the 800-900 nm near-infrared region.

When the aqueous solution for cleaning via irradiation with ultraviolet ray and/or near-ultraviolet visible ray and/or ray in the 800-900 nm near-infrared region according to this embodiment is used for cleaning teeth, for example it is conceivable to construct a dental treatment apparatus comprising a scaler tip which injects an aqueous solution for cleaning via irradiation with ultraviolet ray and/or near-ultraviolet visible ray and/or ray in the 800-900 nm near-infrared region as well as ultraviolet ray and/or near-ultraviolet visible ray and/or ray in the 800-900 nm near-infrared region, and to carry out cleaning by injecting an aqueous solution for cleaning via irradiation with ultraviolet ray and/or near-ultraviolet visible ray and/or ray in the 800-900 nm near-infrared region as well as ultraviolet ray and/or near-ultraviolet visible ray and/or ray in the 800-900 nm near-infrared region at the same time from the tip of the scaler tip.

When such a configuration is taken, in the scaler tip, at least the inner face of the flow pass of the aqueous solution for cleaning via irradiation with ultraviolet ray and/or near-ultraviolet visible ray and/or ray in the 800-900 nm near-infrared region is preferably a nonmetallic face, because metal ions enhance decomposition of hydrogen peroxide.

The concentration of hydrogen peroxide aqueous solution is more preferably 2 w/v % to 6 w/v %, most preferably 3 w/v % and a range of plus/minus about 20% thereof. This is because the concentration can sufficiently generate hydroxyl radicals, and furthermore sufficiently maintain the quality for a long period (about 3 years or longer) even when the amount of the stabilizer is very small.

Embodiment 2

The dentifrice for cleaning via irradiation with ultraviolet ray and/or near-ultraviolet visible ray and/or ray in the 800-900 nm near-infrared region according to this embodiment is characterized in that the concentration of hydrogen peroxide is 1 w/v % to 7 w/v % with respect to the dentifrice base, and only 81 ppm or lower of hydrogen peroxide stabilizer is contained in the base. The hydrogen peroxide stabilizer and the impurity heavy metals in the dentifrice for cleaning via irradiation with ultraviolet ray and/or near-ultraviolet visible ray and/or ray in the 800-900 nm near-infrared region according to this embodiment can be explained in the same way as described in Embodiment 1.

When the dentifrice for cleaning via irradiation with ultraviolet ray and/or near-ultraviolet visible ray and/or ray in the 800-900 nm near-infrared region according to this embodiment is used for teeth cleaning, for example a user applies the dentifrice on a brush portion of a toothbrush having an ultraviolet ray- and/or near-ultraviolet visible ray- and/or 800-900 nm near-infrared region ray-emitting section for emitting ultraviolet ray and/or near-ultraviolet visible ray and/or ray in the 800-900 nm near-infrared region from a bristle area, and the user brushes the teeth while irradiating the dentifrice with ultraviolet ray and/or near-ultraviolet visible ray and/or ray in the 800-900 nm near-infrared region, so that the oral cavity can be sterilized at the same time as teeth cleaning.

As an abrasive, calcium hydrogen phosphate, calcium carbonate, aluminum hydroxide and the like are contained. They are chemically stable, and do not react with hydrogen peroxide nor deteriorate by laser irradiation. As a foaming agent, lauroyl sarcosine soda and sodium lauryl sulfate are contained. This is because they also do not deteriorate by laser irradiation with ultraviolet ray and/or near-ultraviolet visible ray and/or ray in the 800-900 nm near-infrared region. In addition, sorbitol, glycerin, propylene glycol and the like as moisturizers, and sodium alginate, carboxymethyl cellulose and the like as binders may be constructed so as to be used after the an irradiation step of the dentifrice for cleaning via irradiation with ultraviolet ray and/or near-ultraviolet visible ray and/or ray in the 800-900 nm near-infrared region according to the present invention with ultraviolet ray and/or near-ultraviolet visible ray and/or ray in the 800-900 nm near-infrared region.

Confirmation of Toxicity of Stabilizer Decomposed Product

1. Preparation of Concentrated Dry Solids of Photo-Irradiated Oxydol Product and Light-Irradiated 3% Hydrogen Peroxide Aqueous Solution 200 µL of each of the hydrogen peroxide aqueous solution F and the hydrogen peroxide aqueous solution J as well as 3% hydrogen peroxide aqueous solution (30% hydrogen peroxide made by SANTOKU CHEMICAL INDUSTRIES Co., Ltd. was diluted 10 times with purified water, without stabilizer) was dispensed to each well of a 96-well microplate, which was irradiated with 405 nm laser (RV-1000, made by Ricoh Optical Industries Co. Ltd.) from above with an output of 600 mW (irradiance: 1800 mW/cm$^2$) for 20 minutes (LD (+) in FIGS. 8 and 9).

This operation was repeated 26 times or more to secure 5 mL or more of each sample. 5 mL of each sample was put into a glass tube and concentrated using an evaporator (Rotary Evaporator RE200, made by Yamato Scientific co., ltd.) at a heating temperature of about 40° C. and a cooling water temperature of about 0° C. In order to decompose hydrogen peroxide remaining in the tube, 200 µL of aqueous solution of 5000 unit/mL catalase (derived from bovine liver, made by Wako Pure Chemical Industries, Ltd.) was dispensed into each tube.

Subsequently, the tube was furthermore subjected to an evaporator to obtain a dry solid.

Figure 8:
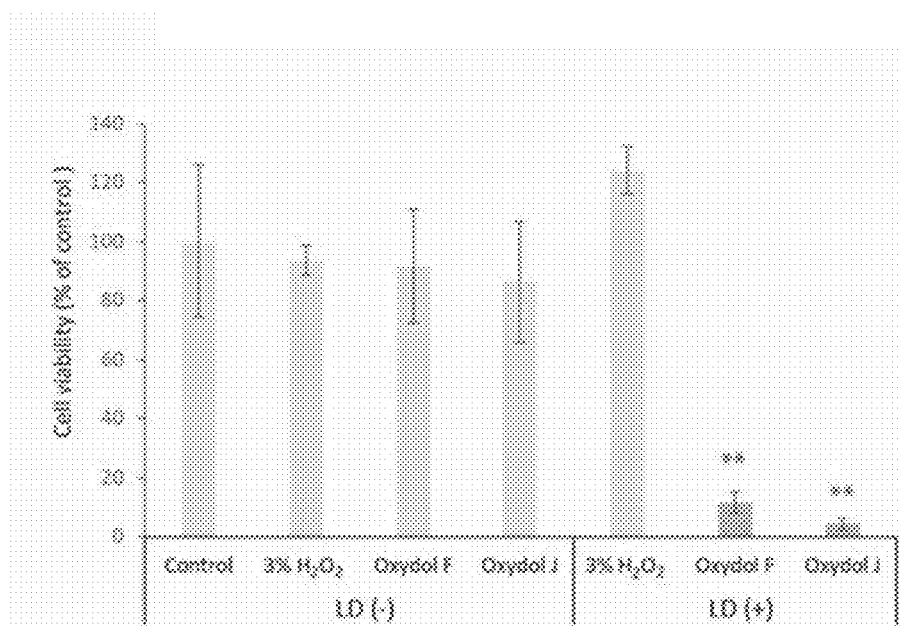
FIG. 8 illustrates a result of the first cytotoxic test for human cells depending on the presence or absence of laser irradiation on the hydrogen peroxide aqueous solution F containing 344 ppm of phenacetin and the hydrogen peroxide aqueous solution J containing 177 ppm of acetanilide.
Figure 9:
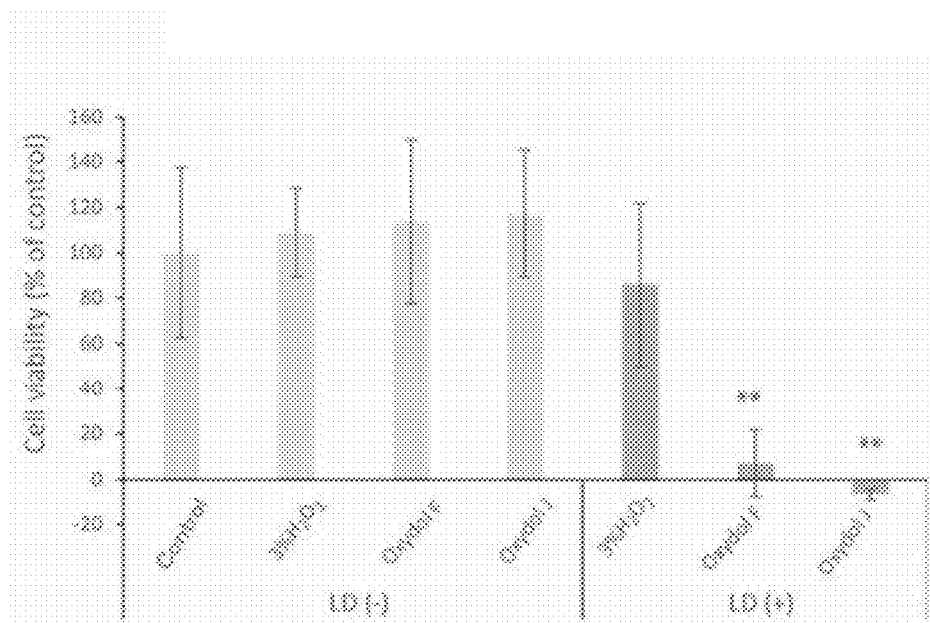
FIG. 9 illustrates a result of the second cytotoxic test for human cells depending on the presence or absence of laser irradiation on the hydrogen peroxide aqueous solution F containing 344 ppm of phenacetin and the hydrogen peroxide aqueous solution J containing 177 ppm of acetanilide.

As comparisons, 5 mL of each of the hydrogen peroxide aqueous solutions F and J as well as 3% hydrogen peroxide aqueous solution without photoirradiation were also treated in the same manner (LD (−) in FIGS. 8 and 9) to obtain a dry solid. 2.5 mL of physiological saline was added to the obtained dry solid, which was dissolved, and sterilized by filtration through a 0.22 μm membrane filter, and this solution was subjected to the test.

2. Influence of Each Sample on Human Gingival Fibroblast in Growth Phase

A human gingival fibroblast (Primary Cell Co., Ltd.) cultured in a 25 cm² flask at 37° C. under a 5% $CO_2$ condition was treated with 0.25% Trypsin-EDTA solution (Life Technologies Corporation), and a cell suspension was prepared in a medium in accordance with a conventional method so that a cell density was $2 \times 10^4$ cells/mL.

Herein, for the medium, a medium prepared by adding a fetal bovine serum (Life Technologies Corporation) and a penicillin/streptomycin solution (10000 units/mL of penicillin and 10 mg/mL of streptomycin, made by Wako Pure Chemical Industries, Ltd.) to Dulbecco's Modified Eagle Medium (DMEM, made by Life Technologies Corporation) so that the fetal bovine serum concentration was 10% (v/v) and the penicillin/streptomycin solution concentration was 1% (v/v), was used as a growth medium.

This cell suspension was seeded in a 96-well microplate at a rate of 100 μL/well. After culture at 37° C. under 5% $CO_2$ condition for about 1 day, each sample was added to wells at a rate of 100 μL/well, and allowed to stand at room temperature for 20 minutes. Each sample was removed, and then the wells were washed with the medium once. The medium was added to the wells at a rate of 100 μL/well, cultured at 37° C. under 5% $CO_2$ condition for another 2 days, and then a degree of cell proliferation was measured by a MTT (methyl thiazolyl tetrazolium) method. Specifically, 10 μL of MTT reagent (Trevigen Inc.) was added to each well after culture, and furthermore cultured at 37° C. under 5% $CO_2$ condition for 2 hours.

After culture, 100 μL of Detergent reagent (Trevigen Inc.) was added to each well, which was allowed to stand under light shielding at room temperature for 2 hours. Then, an absorbance at 595 nm was measured using a microplate reader (FilterMax F5, made by Molecular Devices, LLC.). Instead of the sample group, a group treated with sterilized physiological saline was tested as a control group, and a ratio (%) of each treatment group when the absorbance of the control group was taken as 100% was calculated. A significant difference from the control group was assayed by Dunnett's multiple comparison analysis method. The test was conducted twice. The results are shown in FIG. 8 (first time) and FIG. 9 (second time).

The physiological saline solutions of the concentrated dry solids of the irradiated hydrogen peroxide aqueous solutions F and J showed very strong cytotoxicity on the human gingival fibroblast in the growth phase by a brief treatment of 20 minutes in both tests. Under the same condition, physiological saline solution of the concentrated dry solid of 3% $H_2O_2$ aqueous solution showed no cytotoxicity.

From the above results, it was confirmed that stabilizers, in particular phenacetin and acetanilide decomposed products resulting from ultraviolet ray and/or near-ultraviolet visible ray and/or ray in the 800-900 nm near-infrared region were toxic to humans.

Generation of Hydroxyl Radicals by Ray in 800-900 nm Near-Infrared Region

Figure 10:
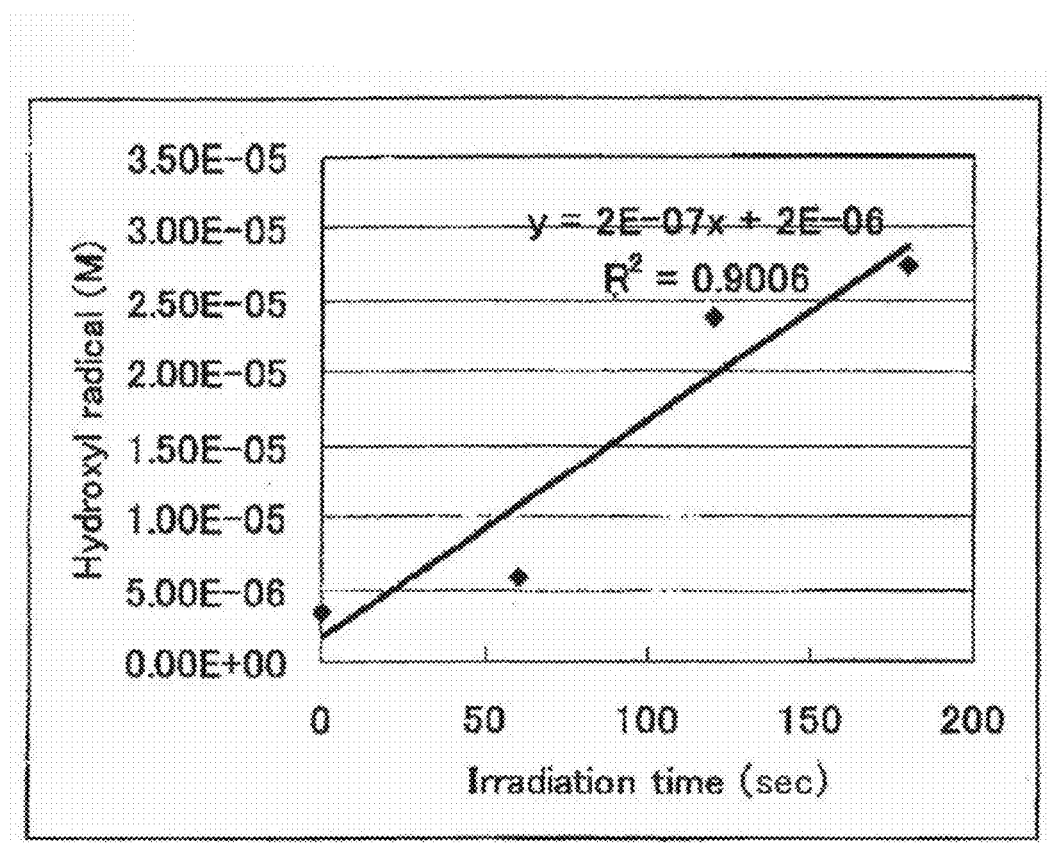
FIG. 10 illustrates a diagram that hydroxy radical generation by ray in an 800-900 nm near-infrared region was confirmed.

In the example of FIG. 10, the experiment was conducted while changing the irradiation time of the laser light. That is, the dependence of hydroxyl radical generation on the photoirradiation time was investigated. In this figure, the case of 1 M is represented by ☐ (white square), and the case of 0.1 M is represented by ◆ (black diamond). Increase of the signal intensity (DMPO-OH) depending on the concentration and the irradiation time was observed. In addition, even in the case of 0.1 M, generation of the hydroxyl radical was observed. This example is a case of irradiation with 805 nm infrared ray. Nine hundred and ninety microliters of the hydrogen peroxide aqueous solution and 10 μL of DMPO were added to a glass cell (diameter: 30 mm, depth: 5 mm) and irradiated with infrared ray of 805 nm. For a laser irradiation apparatus using infrared ray, an apparatus made by UNITAC Co., LTD. was used. Before the photoirradiation, 5 μM of hydroxyl radical was contained. After the photoirradiation, the hydroxyl radical was linearly increased at a rate of 2 μM per 10 seconds. It was found that irradiation for 25 seconds or longer was preferable for generating 10 μM of hydroxyl radical. When hydrogen peroxide (1M) was irradiated with infrared ray (805 nm), the hydroxyl radical was clearly generated. Furthermore, in the near-infrared ray region, rays at 800 to 900 nm are more preferable. This is because, in the range of 800 to 900 nm, the amount of the generated hydroxyl radical is remarkably increased compared to other ranges.

What is claimed is:

1. A method for cleaning teeth, comprising:
   injecting an aqueous solution for intraoral cleaning via irradiation with an ultraviolet ray and/or a near-ultraviolet visible ray and/or a ray in an 800-900 nm near-infrared region,
   wherein the aqueous solution includes:
      hydrogen peroxide, a concentration of the hydrogen peroxide in the aqueous solution being in a range of 1 w/v % to 7 w/v %;
      water containing iron and coper as impurities, an amount of each of the iron and the copper being less than 0.05 mg/L in the water; and
      a hydrogen peroxide stabilizer, a concentration of the hydrogen peroxide stabilizer in the aqueous solution being 81 ppm (mg/L) or less, the hydrogen peroxide stabilizer being at least one of a group consisting of phosphoric acid, phenacetin, and acetanilide,
   after the ultraviolet ray and/or the near-ultraviolet visible ray and/or the ray in the 800-900 nm near-infrared region irradiates the aqueous solution for five minutes, there is no decomposed products that are toxic to a human in the aqueous solution via a high performance liquid chromatography analysis, and
   a content of impurity heavy metals, which decompose the hydrogen peroxide, in the aqueous solution is 0.001 w/v % or less with respect to the hydrogen peroxide, and
   the hydrogen peroxide stabilizer is configured to prevent the hydrogen peroxide from being decomposed by the impurity heavy metals.

2. The method according to claim 1,
   wherein the concentration of the hydrogen peroxide in the aqueous solution is in a range of 2 w/v % to 6 w/v %.

3. The method according to claim 1,
   wherein the concentration of the hydrogen peroxide in the aqueous solution is in a range of 2.4 w/v % to 3.6 w/v %.

* * * * *